United States Patent
Miyajima

(10) Patent No.: US 7,183,909 B2
(45) Date of Patent: Feb. 27, 2007

(54) INFORMATION RECORDING DEVICE AND INFORMATION RECORDING METHOD

(75) Inventor: Yasushi Miyajima, Kanagawa (JP)

(73) Assignee: Sony Corporation (JP)

( * ) Notice: Subject to any disclaimer, the term of this patent is extended or adjusted under 35 U.S.C. 154(b) by 174 days.

(21) Appl. No.: 10/941,515

(22) Filed: Sep. 15, 2004

(65) Prior Publication Data

US 2005/0088297 A1    Apr. 28, 2005

(30) Foreign Application Priority Data

Oct. 6, 2003    (JP) ............................ P2003-347446

(51) Int. Cl.
*G08B 1/08* (2006.01)
(52) U.S. Cl. .............................. 340/539.12; 340/539.1; 340/539.11; 340/573.1; 340/825.36; 340/825.49; 340/825.69
(58) Field of Classification Search ........... 340/539.12, 340/539.1, 539.11, 539.13, 539.19, 825.36, 340/825.49, 825.69, 407.1; 600/300, 301, 600/322; 128/903, 920
See application file for complete search history.

(56) References Cited

U.S. PATENT DOCUMENTS

| | | | |
|---|---|---|---|
| 6,198,394 B1 * | 3/2001 | Jacobsen et al. ......... | 340/573.1 |
| 6,605,038 B1 | 8/2003 | Teller et al. ................ | 600/300 |
| 6,847,892 B2 * | 1/2005 | Zhou et al. .................. | 701/213 |
| 6,954,148 B2 * | 10/2005 | Pulkkinen et al. ........ | 340/572.1 |
| 2001/0049471 A1 | 12/2001 | Suzuki et al. ............... | 600/300 |
| 2002/0024450 A1 | 2/2002 | Townsend et al. ...... | 340/870.16 |
| 2002/0188214 A1 | 12/2002 | Misczynski et al. ........ | 600/516 |

FOREIGN PATENT DOCUMENTS

EP    0976360    2/2000

* cited by examiner

*Primary Examiner*—Hung Nguyen
(74) *Attorney, Agent, or Firm*—Lerner, David, Littenberg, Krumholz & Mentlik, LLP

(57) ABSTRACT

An information recording device and a method of recording the information, in which the state around a user may be recorded efficiently includes a change sensor that maps three sorts of bio-information, as measured by a bio-information sensor, namely the number of heart beats, GSR (galvanic skin response), and the skin temperature difference, in a three-dimensional feature space, as observed values, and generates classes on the three-dimensional feature space. The change sensor compares a class to which a newly measured observed value belongs to a class to which belong the values measured in the past in order to detect a change in the user when the classes differ from each other. On detection of the changes by the change sensor, a controller actuates a video camera, a still camera, and a microphone to record the image and the sound around the user.

14 Claims, 5 Drawing Sheets

LIST OF RECORDING CONTENTS

| TIME | POSITION | MEASURD VALUES | NAMES |
|---|---|---|---|
| 2003/05/03 22:11 | XXXX KITA-SHINAGAWA, SHINAGAWA-KU, TOKYO | STATE C | THROBBING |
| 2003/05/03 23:05 | MMMM KITA-SHINAGAWA, SHINAGAWA-KU, TOKYO | STATE B | LARGE SOUND |
| 2003/05/04 10:08 | XXXX SUGAMO TOSHIMA-KU, TOKYO | BREATHING | DEEP BREATHING |
| ...... | ...... | ...... | ...... |

FIG. 3

INFORMATION RECORDING DEVICE AND INFORMATION RECORDING METHOD

BACKGROUND OF THE INVENTION

1. Field of the Invention

This invention relates to an information recording device and method of recording the information for automatically recording the state around a user.

This application claims priority of Japanese Patent Application No.2003-347446, filed in Japan on Oct. 6, 2003, the entirety of which is incorporated by reference herein.

2. Description of Related Art

Recently, a mobile bio-information sensor or a mobile environmental sensor has been developed, in keeping up with the progress in the field of the sensor and with the reduction in size of information equipment. The bio-information sensor is a sensor used for measuring the bio-information of the user. The bio-information quantitatively specifies the movements of various organs of the living body, such as the number of heart beats or the brain wave. A small-sized bio-information sensor may be worn by a user to measure the user's bio-information which may then be analyzed to detect the emotion or changes in the physical state of the user. The environmental sensor is a sensor used for measuring the environment around the user, such as weather, atmospheric temperature or noise. The noise generated or changes in the weather indicate that some change has occurred around the user.

There has so far been known an information processing device for recording the user's bio-information or the environmental information to aid in the power of memory of the user. For retrieving the target information from the recorded information, a histogram or a distribution curve is generated for the totality of the time period in which the bio-information has been recorded to exploit the meaning in the bio-information sensor parameter in the histogram or in the distribution curve (see for example the Patent Publication 1).

[Patent Publication 1] Japanese Laid-Open Patent Publication 2002-236698

The information processing device, stated in the Patent publication 1, records the bio-information or the environmental information at all times, thereby increasing the quantity of the information to be recorded and consumption of the recording resources. On the other hand, if a large quantity of the information is recorded, the processing volume in retrieving the target information is increased to increase the processing load or to prolong the processing access time.

SUMMARY OF THE INVENTION

In view of the above-depicted problems of the prior art, it is an object of the present invention to provide an information recording method and an information recording device whereby the state around the user may be recorded efficiently.

In one aspect, the present invention provides an information recording device comprising acquisition means for acquiring the information, measurement means for measuring the bio-information of a person and/or the environmental information around the person, change detection means for detecting changes in the bio-information or the environmental information, as measured by the measurement means, and recording controlling means for causing recording means to record the information, acquired by the acquisition means, when the change detection means has detected changes in the bio-information or the environmental information.

In another aspect, the present invention provides a recording method comprising the steps of a measurement step of measuring the bio-information of a person and/or the environmental information around the person, a change detection step of detecting changes in the bio-information and/or the environmental information, and a recording step of recording the bio-information and/or the environmental information when the change detection step has detected changes in the bio-information and/or the environmental information.

According to the present invention, the image and/or the sound around the user is recorded when the bio-information and/or the environmental information of the user is changed. Thus, the quantity of the information recorded is decreased compared to that in case the information is recorded at all times. The state around the user is recorded when the bio-information and/or the environmental information of the user are changed, so that the impressive information is recorded to a high probability.

Moreover, according to the present invention, the timing or the site of the recording of the image or the sound, the person who was the user's company at the time of the recording, and so forth, are recorded, in addition to the image or the speech. Thus, the viewer may readily be reminded of what was going on when the recording was made, and hence may retrieve the targeted information by having reference to the recording.

By displaying the time or the site of the recording of the information, the person who was the user's company at the time of the recording, the bio-information or the environmental information changed, the user may reflect the happening of the day or may be fortuitously reminded of what he/she forgot.

BRIEF DESCRIPTION OF THE DRAWINGS

FIG. 3 shows an example of a display image surface demonstrating the synopsis of stored contents in a list form.

DESCRIPTION OF THE PREFERRED EMBODIMENTS

Figure 1:
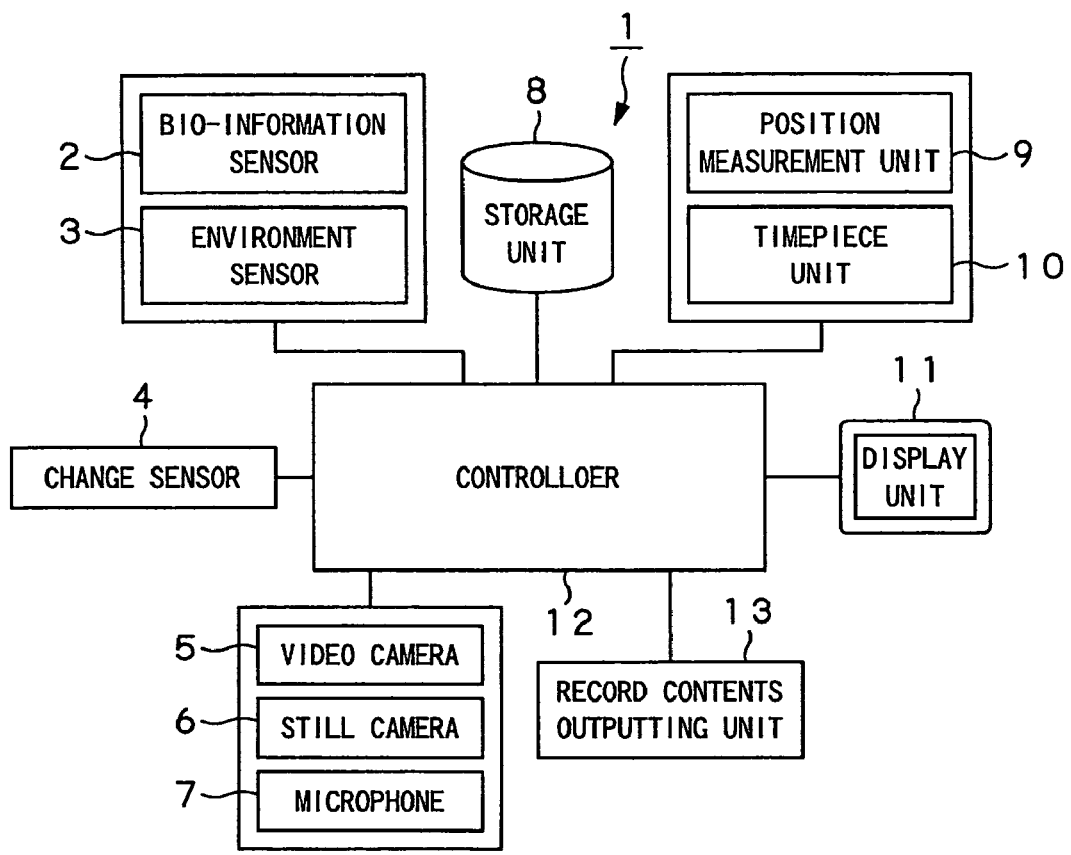
FIG. 1 is a block diagram showing the structure of an information recording device.

1. Embodiment of the Information Recording Device

Referring now to the drawings, an information recording device of the present invention is explained in detail. The information recording device, embodying the present invention, is featured by automatically detecting intrinsic and extrinsic changes in the user to record images or sound around the user responsive to these changes.

FIG. 1 is a block diagram showing the structure of an information recording device 1 according to the present invention. The information recording device 1 includes a bio-information sensor 2, an environment sensor 3 for measuring the environmental information around the user, a change sensor 4 for detecting the intrinsic and extrinsic changes in the user, a video camera 5 for photographing a still image, a still camera 6, a still camera 6 for photographing a still image, a microphone 7 for picking up the sound, a storage unit 8 for storing the image or the speech, a position measurement unit 9 for measuring the user position, a timepiece unit 10 for time-keeping, a display unit 11 for demonstrating the image or the text, and a controller 12 for controlling the information recording device 1.

The bio-information sensor 2 measures the bio-information of the user. The bio-information is mainly the information indicating the intrinsic state in the user. Of course, the bio-information sensor 2 may be constructed discretely from the information recording device 1 and mounted to e.g. the body surface of the user to transmit the bio-information to the information recording device 1 in the wired or wireless transmission configuration. The bio-information sensor 2 is provided on the surface of the information recording device 1 or within the information recording device 1. The bio-information sensor 2 is provided on the surface of the information recording device 1 or within the information recording device 1. The bio-information may be enumerated by breathing, blood oxygen saturation, amount of sweat, heart beat, pulsation, breathing, wink, eye-ball movement, gazing time, pupil diameter, blood pressure, brain wave, body movement, posture, skin temperature, GSR (galvanic skin response), MV (micro-vibration), EMG (electro-myography) and blood oxygen saturation (SPO2). These data may be measured by cardiographic measurement units, EMG measurement units, head electrical voltage measurement units, infrared image intensity analyses, pressure sensors, temperature sensors or sweating sensors.

The environment sensor 3 is used for measuring the environmental information around a person carrying out the measurement operations. The environmental information is mainly the information specifying the extrinsic state of the user, and may be enumerated by temperature, humidity, weather, wind speed, time, lightness, smell, altitude, sound volume, atmospheric pollution, latitude, longitude, movement speed, acceleration, age of the moon, gravity or amount of vibration. These may be measured by lightness meters, gas sensors, thermometers, barometers, rain drop sensors, altimeters, timepieces, noise sensors, atmospheric pollution sensors, or GPS (global positioning system). Similarly to the bio-information sensor 2, the environment sensor 3 may be provided to the main body unit of the information recording device 1 or provided as a discrete component.

The change sensor 4 detects intrinsic changes or extrinsic changes in the user, with the aid of pattern recognition. The pattern recognition is the processing of classifying the subjects of recognition into plural classes, mapping the values being observed in a feature space by coordinate plotting, and associating the subject of recognition with one of the plural classes. The classes are generated by learning from previously collected observed values. The methods for mapping and classifying the observed values will be explained subsequently.

When the change sensor 4 has detected changes, the controller 12 actuates at least one of the video camera 5, still camera 6 and the microphone 7 to record prevailing output values of the respective sensors, in the storage unit 8, along with the images or sound, specifying the status around the user when the changes have occurred. The controller 12 also acquires the user's position and the current time from the position measurement unit 9 and from the timepiece unit 10, respectively, to record the so acquired data in the storage unit 8 along with the images and the sound. The position measurement unit 9 may also acquire the position information not by the aforementioned method of acquiring the position information by the GPS, but by a method consisting in connecting to access points for wireless communication, also termed hot spots. Moreover, if the present device has the function as the mobile phone, the device is able to acquire the position information, which may then be used. The recorded image or speech recorded is referred to below as contents.

The display unit 11 demonstrates the image or the sound, recorded by the storage unit 8, under control by the controller 12, in order to permit the user to monitor the image or the sound. The display unit 11 is also used to demonstrate the operating information of various sorts or the control information.

A record contents outputting unit 13 is responsive to the user's command, entered by an operating unit, not shown, to output the recorded contents in a preset format. The outputting format will be explained subsequently.

In the bio-information and the environmental information, the wink, eye-ball movements, gaze time, pupil diameter, body movements, posture, lightness or the sound volume may be acquired from the video camera 5 or the microphone 7. If these are the subjects for observation, the bio-information sensor 2 or the environment sensor 3 may be omitted.

With the information recording device 1 of the present embodiment, made up by the above blocks, the bio-information of the user is observed by the bio-information sensor 2, the environmental information around the user is observed by the environment sensor 3, the observed values are mapped by the change sensor 4 on the feature space, and signals from an input device, such as the video camera 5, still camera 6 or the microphone 7, are recorded on the storage unit 8 in case it is detected that the observed values have been transferred from a given class to another class. Since the user position as well as the recording time is recorded simultaneously, retrieval at the time of the subsequent reproduction may be carried out extremely readily.

If it is desired to record the image or the sound, as from the time immediately before and inclusive of the time of detection of changes in the observed value of the bio-information or the environmental information, it is sufficient to record the image or the sound previous to the time point of change of the observed value at all times in a ring buffer type memory to transfer the image or the sound to the storage unit 8 for recording the image or the sound therein. This memory may be provided within the controller 12 or formed as an area reserved in the storage unit 8.

1-1 Mapping and Classification of Observed Values

Figure 2:
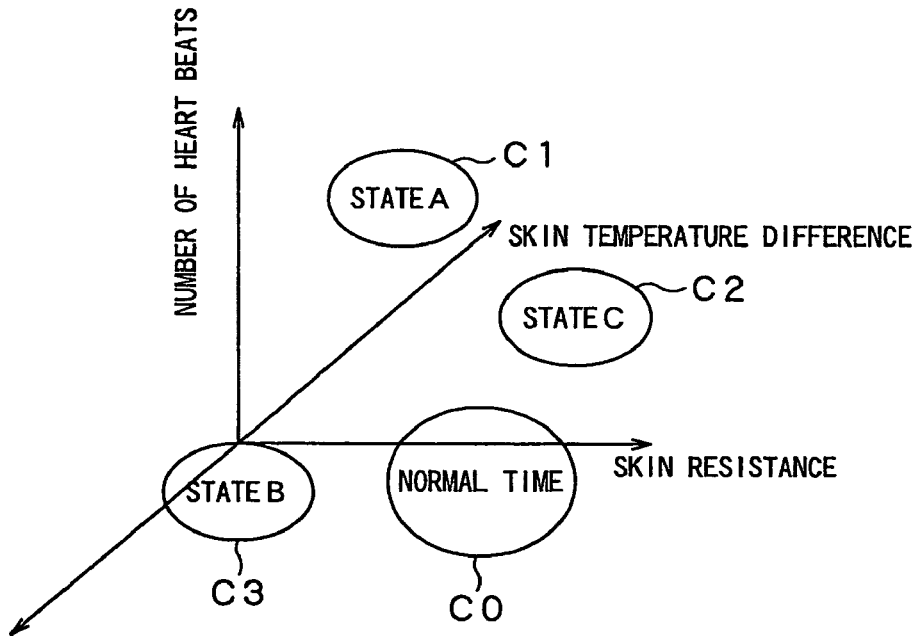
FIG. 2 shows an example of a feature space.

FIG. 2 shows an example of mapping the three sort of the bio-information, that is, the beat of heart, GSR (galvanic skin response) and the skin temperature difference, as observed values in the three-dimensional feature space. Here, a class C0, denotes the usual state of the user, and three classes C1 to C3 denote other states. It is assumed that, for simplicity of explanation, and for convenience in formulating the drawings, the number of classes is four, with the classes being spaced apart sufficiently from one another. However, the classes may be close to one another, or four or more sorts of the classes may be used. In FIG. 2, the newly measured bio-information may belong to one of these four classes C0 to C3, or of a class different from any of these classes.

Each time a new observed value is entered, the change sensor 4 verifies to which of the classes C0 to C3 belongs this observed value. The change sensor 4 compares the class to which belongs the new observed value and the class to which belongs the observed value entered ahead of the new observed value. If these classes differ from each other, the change sensor 4 verifies that the user state has changed. Moreover, if the observed value belongs to none of the classes, the change sensor 4 verifies that the user state has changed. That is, if the feature space area, not belonging to the classes C0 to C3, is also a class, the change sensor verifies that the user state has changed when the new observed value is entered and mapped in the feature space, and when the observed value has shifted from the class to which it belonged to another class.

The change sensor 4 allocates the observed value to the class and learns the relationship of correspondence between the observed value and the class as knowledge. By repetition of this learning, it is possible to generate the feature space suited to the user. For example, if the skin temperature is the observed value, the area of the observed values during the normal time period, termed the cool fever, may be defined as class C0. However, this normal value not only differs from user to user, but also is changed, even with the same user, depending on time of measurement and season. There are also occasions where accidental noise is introduced into the observed values, depending on the sensor type or the method for mounting the sensor. These noises are preferably not used as the subject of observation. Thus, when the observed values are plotted on the feature space, by way of mapping, it is desirable to find the state of distribution of the observed values, that is, the density or variance, during a certain time period, and to re-define and update the area of high density as a class.

Although the status change is detected with the values of the three sort of the bio-information as observed values, the feature space may also be formed with other sorts of the bio-information or the environmental information as observed values. It is also possible to change the number of the observed values to generate the feature space with the different number of the dimensions, such as seven-dimensional or eight-dimensional feature space. In addition, a large number of the feature spaces may be generated simultaneously.

The change sensor 4, embodying the present invention, roughly classifies the intrinsic state and the extrinsic state of the user, depending on the distribution of the observed values, and records the image or the sound, with the state transition from a given class to another class as a trigger. Since the purport of the present invention resides in recording the state around the user, with the change in the status as a trigger, such as to record necessary scenes efficaciously, there is no necessity of analyzing what is the current status of the user.

1-2 Other Method for Change Detection

Two other change detection methods are hereinafter explained. With the first method, the same observed values, as obtained at different time points, are compared to each other, and a change is detected when the difference between the observed values exceeds a preset threshold value. In case the observation is carried out at a preset time interval, the difference or offset between the last observed value and the outstanding observed value, is found, such that, in case the difference is large, a decision is given that the state of the user has changed. Of course, if the observed value is an analog value, its difference or partial difference may be found. If, for example, the video camera 5 or the microphone 7 is actuated when the heart beat has changed, it is possible to acquire an image when the user is doing exercise or when the user is in tension.

However, the body temperature, lightness or the altitude is an observed value changed only gradually. If such observed value, changed only gradually, is compared at a short time interval, it is impossible to detect changes. Thus, the time interval for change detection is set, and a status change is deemed to have occurred when the difference between the current value of measurement and the value obtained the preset time duration before is larger than a threshold value. The time duration or the threshold value may be fixed or updated by learning.

With the second method, the change in the user is detected depending on whether or not the observed value exceeds a preset threshold value. For example, the human does not gaze at a subject in which he/she is not interested. If the gaze time duration of the user is long, it is highly likely that the user's attention is concentrated in some subject. Thus, if the video camera 5 or the still camera 6 is actuated in case the gazing time exceeds the preset time, the subject which is of interest for the user may be imaged. On the other hand, no unusually large sound is generated during the normal life of the human being. Thus, if the large sound is produced, the probability is high that some accident or happening has occurred. Hence, if a sound larger than a preset threshold value is produced, the video camera 5 or the still camera 6 may be actuated to image a scene of bung-ho in a banquet or the site of accident. The threshold value need not be fixed and may be changed from user to user.

1-3 Method for Outputting Record Contents

The configuration of recording the information around the user has so far been explained. The ensuing description is directed to the method of outputting the recorded information in a state which will facilitate the retrieval by the user. The record contents outputting unit 13 outputs the recorded contents in a preset form in keeping with the command by the user. FIG. 3 depicts an image surface 41 output in a list form. In the instant example, the time and the place of the contents recording, and the sorts of the measured value changed, are displayed. If the contents are a moving picture or the sound, the recording start time and the recording end time may be displayed, or the recording start time and the recording time, may be displayed. This list is an image surface for notifying for the user which contents are stored, and is also an input image surface accepting a command to output the stored data. The user specifies the contents for display, by actuation of a pointing device or a cross-key. The record contents outputting unit 13 then outputs the specified contents. Of course, the specified contents may be demonstrated on the display unit 11.

Figure 4:
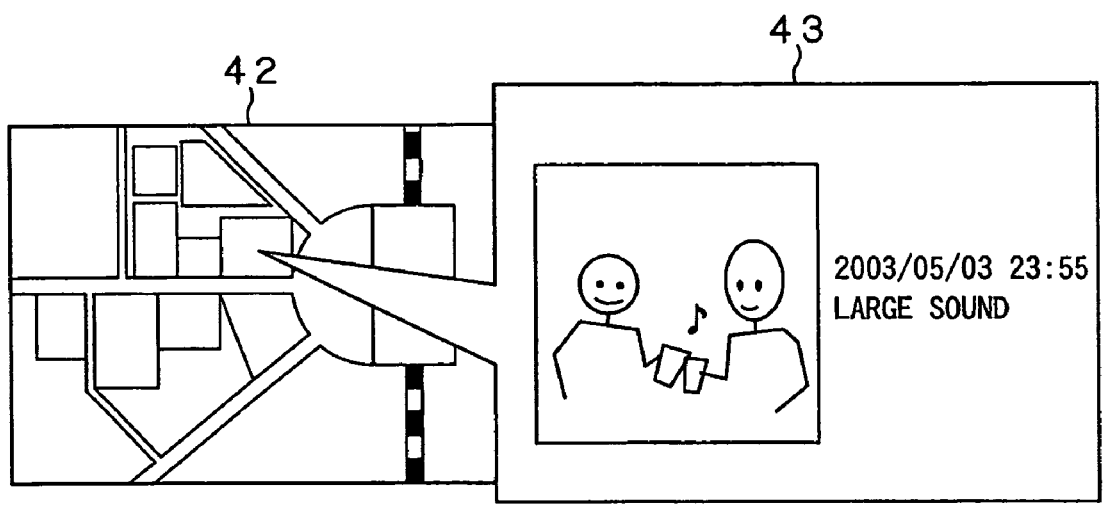
FIG. 4 shows an example of a display image surface demonstrating the recording positions of contents on a map.

FIG. 4 depicts an image surface 42 demonstrated as a map. On the map of FIG. 4, there is entered a symbol indicating the record locations for the contents. The symbol may also be the name of the contents, the time of recording the contents, the number of contents recorded or the sort of the observed value changed. When the user has selected the symbol on the map, the record contents outputting unit 13 outputs contents 43 corresponding to the positions on the map.

Figure 5:
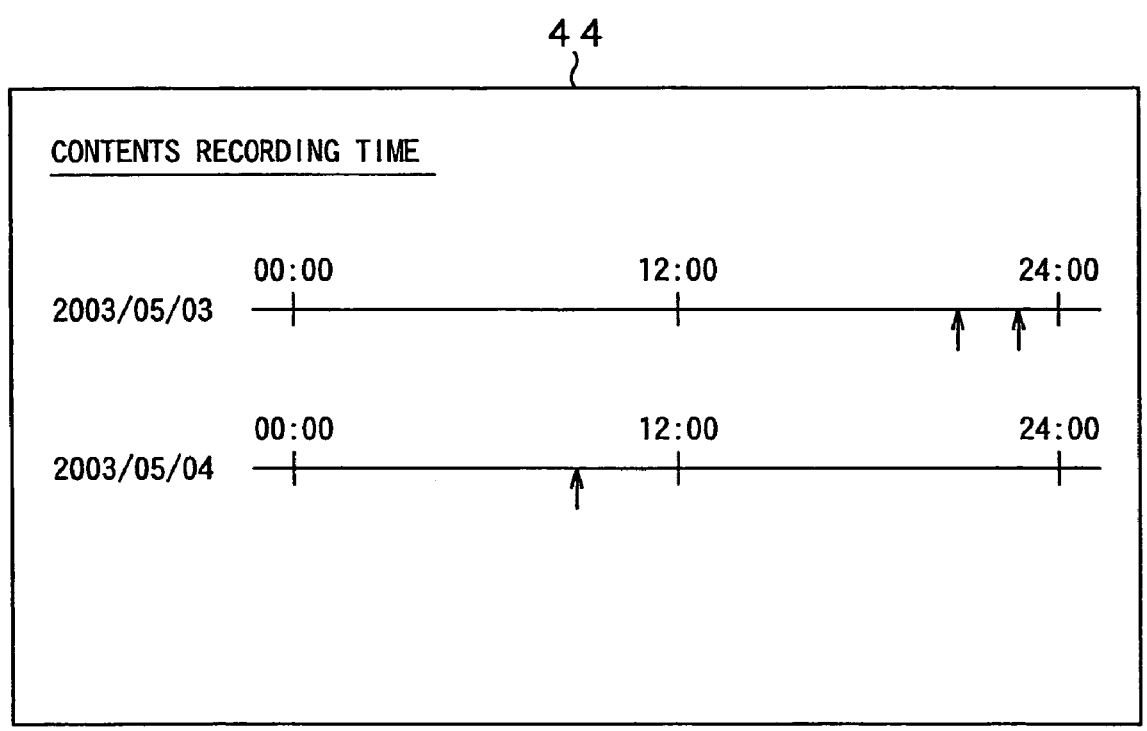
FIG. 5 shows an example of a display image surface demonstrating the recording positions of contents along time axis.

FIG. 5 depicts an image surface 42 when displayed in the map form. On the map of FIG. 4, a symbol indicating the contents record location is displayed. The symbol may also be the name of the contents, the time of recording the contents, the number of contents recorded or the sort of the observed value changed. When the user has selected the symbol on the time axis, the corresponding contents are displayed. The time-axis type display may also be an image surface on a calendar or on a timepiece.

It is noted that, when outputting the sort of the observed value, the record contents outputting unit 13 converts the output into a term more intelligible for the user and outputs the resulting term. For example, if the amount of the breathing by the user is high, the state is not expressed simply as 'breathing' but as 'deep breathing'. Such terms as 'angry' or 'surprised' may also be used for expression, responsive to the user's emotion as detected from the state of change of the observed value or the state of class-to-class transition.

As described above, the information recording device 1 according to the present invention is featured by the fact that the image or the sound around the user is recorded when the intrinsic or extrinsic state of the user has been changed. Since the present information recording device 1 records the information at preset timing, the recording capacity as needed is smaller than that in case of continuous recording. Moreover, data retrieval is facilitated by recording only the needed contents.

In addition, since the information recording device 1 records the time and date of contents recording and the contents recording location, along with the contents, it becomes possible to use the contents as index for retrieval or for putting the contents in order.

2. Embodiment of Mobile Terminal

A mobile terminal 20, embodying the present invention, is hereinafter explained. This mobile terminal 20 is designed to provide the aforementioned information recording device 1 with the function of exchanging the information with another mobile terminal 20.

Figure 6:
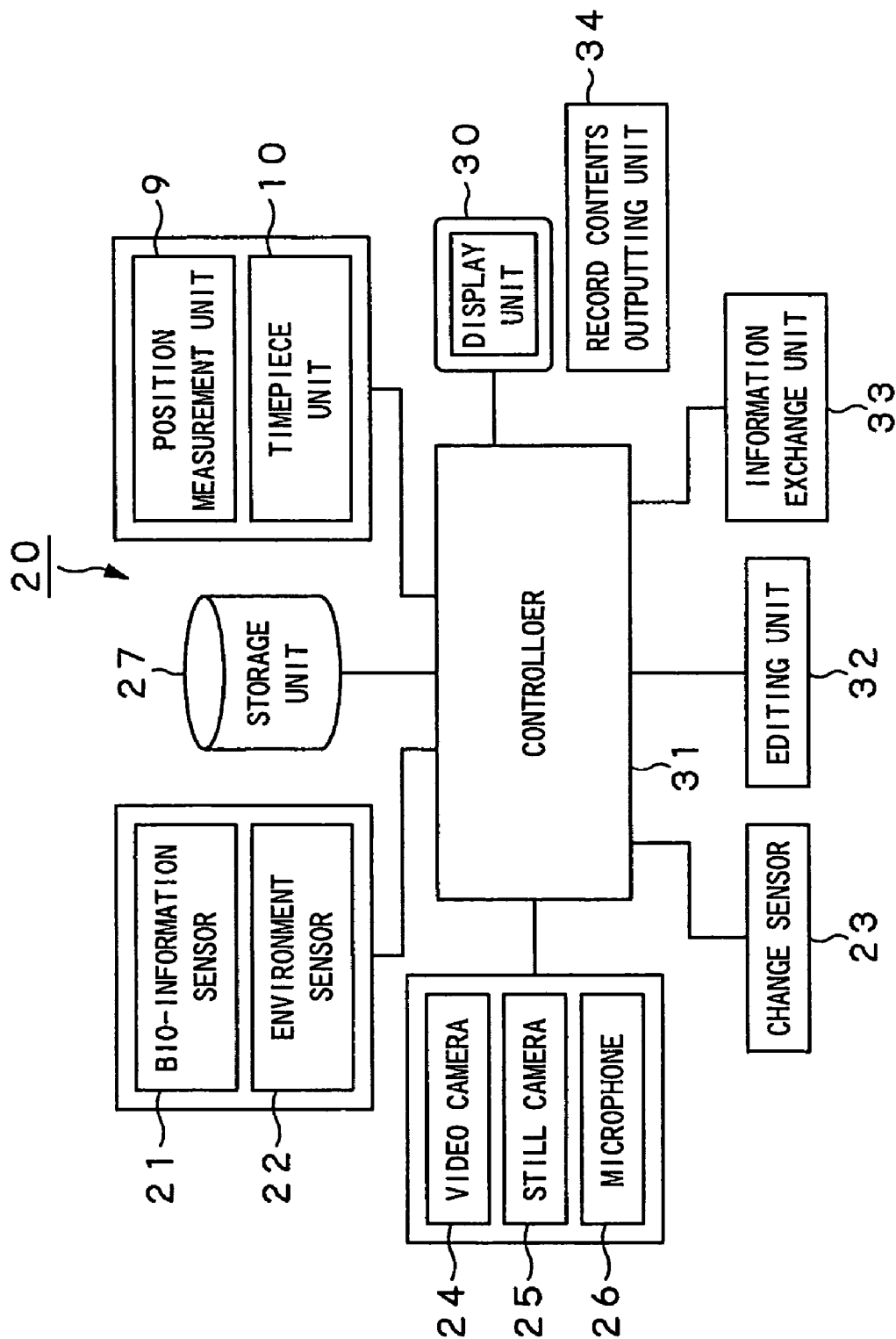
FIG. 6 is a block diagram showing the structure of a mobile terminal.

FIG. 6 depicts a block diagram showing the configuration of the mobile terminal 20. Similarly to the information recording device 1, the mobile terminal 20 includes a bio-information sensor 21 for measuring the user's bio-information, an environment sensor 22 for measuring the environmental information around the user, a change sensor 23 for detecting the intrinsic and extrinsic changes in the user, a still camera 25 for photographing a still image, a video camera 24 for photographing a moving picture, a microphone 26 for picking up the sound, a storage unit 27 for storing the image or the speech, a position measurement unit 28 for measuring the user position, a timepiece unit 29 for time-keeping, a display unit 30 for outputting the recorded contents, and a controller 31 for controlling the information recording device 20 in its entirety. These blocks perform the same operations as those of the corresponding blocks of the information recording device 1 and hence the explanation thereof is omitted for simplicity.

The mobile terminal 20 also includes an editing unit 32 for editing the recorded information and an information exchange unit 33 for exchanging the information with other mobile terminals 20.

The editing unit 32 records contents attributes, such as names of the contents recorded, or names of persons recorded in the contents. The contents attributes, entered automatically, as explained later, may also be entered by the user.

The information exchange unit 33 includes communication means designed in accordance with the near-distance wireless technique, such as Bluetooth. If users in possession of the mobile terminals 20 of the same sort are close to each other, the mobile terminals 20 may be interconnected wirelessly to enable e.g. P2P communication. That is, the contents or various information sorts, recorded in other mobile terminals 20, may automatically be acquired on the side of the mobile terminal 20.

In the storage unit 27, the private information of the user, as the owner of the mobile terminal 20, is recorded, in addition to the aforementioned image or sound. Examples of the recordable private information include the name, age, mail address, telephone number or the face image.

Figure 7:
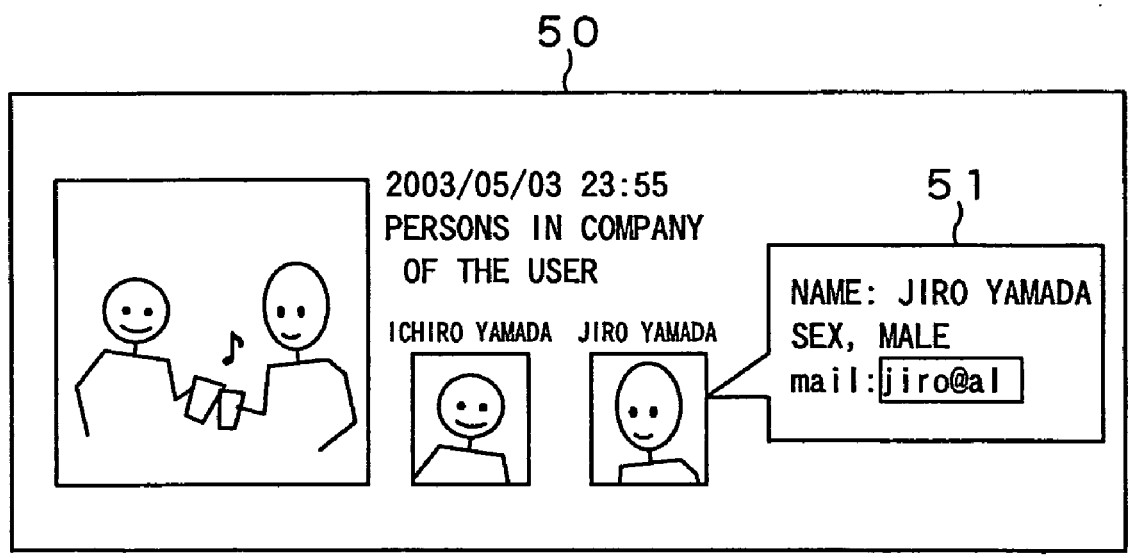
FIG. 7 shows an example of an input image surface for inputting the attributes of contents.

An instance of inputting contents attributes is now explained. The contents of FIG. 7 show how a banquet is going on. In this mobile terminal 20, an image or the speech is recorded responsive to status changes in the user. For example, the images or the sound on the site is recorded, with the sound of the bung-ho as a trigger. Since the mobile terminals 20, owned by plural users, are close to one another, these terminals are wirelessly interconnected by communication means of the information exchange unit 33. Thus, the private information of the users, recorded in the respective mobile terminals 20, or the recorded contents, are exchanged. The private information transmitted is correlated with the image or the sound recorded and is recorded in the so correlated state in the storage unit 27.

Figure 8:
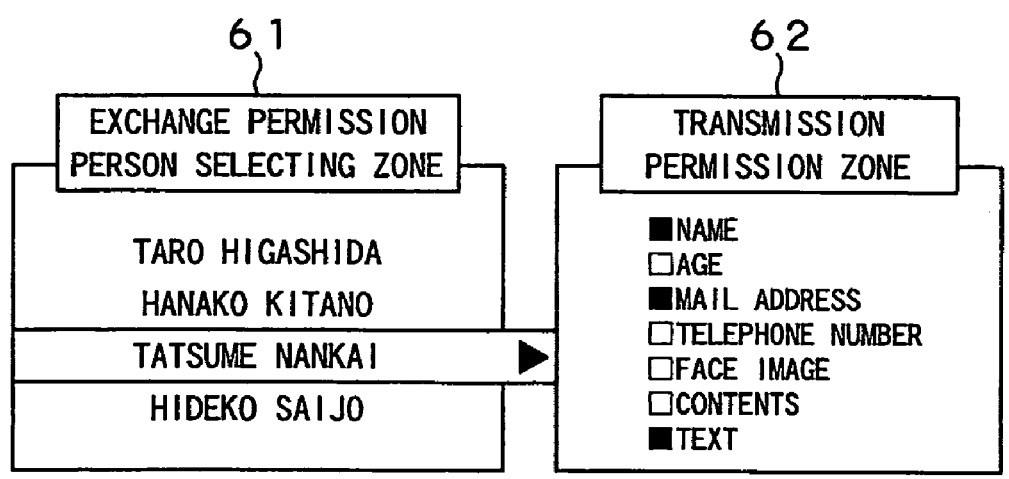
FIG. 8 shows an example of an input image surface for inputting the transmission permitting information.

In the exchange of the private information or the contents, it is not desirable to transmit any information irrespective of the counterpart of communication. Thus, the information exchange unit 33 is provided with the exchange permission information for limiting the information transmission. The information exchange unit 33 is supplied with the exchange permission information for users and executes information exchange with other users in accordance with the exchange permission information. This exchange permission information states the person who supplies the information and the sort of the information supplied. The exchange permission information is entered by the user and recorded in e.g. a preset area of the storage unit 27. In an input image surface of the exchange permission information, there is displayed a person selecting zone 61 for selecting the person allowed for transmission, as shown in FIG. 8. When the user selects the person, allowed for transmission, an item selection zone 62 for selecting the items of transmission permission is displayed. When the user has selected the person allowed for transmission, the item selection zone 62 for selecting the items that can be transmitted, such as name, age, mail address, telephone number, facial image, contents or text, is displayed. The contents are those recorded in the mobile terminal 20, while the text is that stating e.g. a message the user imparts to the user of the destination of the transmission. The user selects the information of transmission from the item selection zone 62.

The information exchange unit 33 verifies whether or not there is any person around the user to whom the information is to be transmitted. If a relevant person is found, the private information of the user is sent to the mobile terminal 20 of the relevant person. The information exchange unit 33 is supplied with the information, specifying the owner, transmitted by a terminal owned by each person, and specifies the person who is on the spot, based on the so received information. The information exchange unit 33 records the private information of other users, received from the other mobile terminal 20, along with the contents. By simultaneously recording the contents and the person in the near-by site, recorded in the contents, the manner in which the contents have been recorded may be recorded in detail. The information exchange unit 33 is also able to transmit the information by broadcasting to all of the persons on the spot.

In the above-described embodiment, the counterpart of the near-distance communication is specified based on the private information of the persons registered in advance in the mobile terminal 20. If a person has not been registered, the user may input it by the editing unit 32, or may have the counterpart party transmit the private information to record the so transmitted information in association with the recorded contents. Alternatively, biometrics may be used to specify a person from the features of the face image or the voice print.

With the mobile phone, according to the present invention, described above, in which the contents, the attributes of the contents and the information pertinent to the person who was in the near-by place when the contents were recorded, are recorded in correlation to one another, the user may be reminded of the scene of the recording of the contents.

In the above-described embodiments, the ecological information (living-body information) pertaining to the user is acquired. The present invention is, however, not limited to this embodiment. For example, the living-body information of the person being imaged may be acquired by the information recording device, operated by the user, or a by a video camera, provided to the mobile terminal.

What is claimed is:

1. An information recording device comprising
acquisition means for acquiring information;
measurement means for measuring bio-information of a person and/or environmental information around said person;
change detection means for detecting changes in said bio-information and/or said environmental information measured by said measurement means;
recording means; and
recording controlling means for causing said recording means to record the information acquired by said acquisition means, when said change detection means detects changes in said bio-information and/or said environmental information,
said change detection means being operable to form classes in a feature space having values of said bio-information and/or the environmental information as observed values, and to detect changes in said bio-information and/or said environmental information when the class to which the bio-information or the environmental information currently measured belongs and the class to which the measured bio-information or the environmental information belongs in the past differ from each other.

2. The information recording device according to claim 1 further comprising time-keeping means,
wherein said recording controlling means causes said recording means to record the time when the bio-information and/or the environmental information has changed.

3. The information recording device according to claim 1 further comprising
position measurement means for measuring a position of said person, wherein
said recording controlling means causes said recording means to record the position of said person at a time when the bio-information and/or the environmental information has changed.

4. The information recording device according to claim 1 further comprising
private information storage means for storing the private information of a user;
storage means for storing identification information of a particular person;
specifying means for specifying a person around the user; and
transmitting means for transmitting the private information of the user to an information communication terminal owned by a person specified to be in a near-by site of the user by said specifying means when said person is a person stored in said storage means.

5. A recording method comprising:
a measurement step of measuring bio-information of a person and/or environmental information around said person;
a change detection step of detecting changes in said bio-information and/or said environmental information; and
a recording step of recording the bio-information and/or the environmental information when said change detection step detects changes in said bio-information and/or said environmental information,
said change detection step forms classes in a feature space having values of said bio-information or the environmental information as observed values, and verifies the classes to which the bio-information or the environmental information as measured in said measurement step belong to detect changes in said bio-information and/or the environmental information when the classes to which the bio-information or the environmental information, as measured at different time points, belong differ from each other.

6. The information recording method according to claim 5 further comprising:
a time-keeping step; and
a step of recording a time when the change is detected in said change detection step.

7. The information recording method according to claim 5 further comprising
a position measurement step for measuring a position of a person; and
a step of recording the position of the person when the change in the bio-information and/or the environmental information is detected in said change detection step.

8. The information recording method according to claim 5 further comprising
a specifying step of specifying a person around a user; and
a transmitting step of transmitting private information of the user to an information communication terminal owned by a person specified to be in a near-by site of the user in said specifying step.

9. An information recording device comprising:
means for measuring bio-information of a person and/or environmental information around said person;
change detection means for detecting changes in said bio-information and/or said environmental information measured by the measuring means;
recording means for recording said bio-information and/or said environmental information; and
recording controlling means for controlling said recording means,
said change detection means being operable to detect changes in said bio-information and/or said environmental information by use of pattern recognition which includes classifying a number of subjects into a number of classes, and mapping an observed value of said bio-information and/or said environmental information into a class in a feature space.

10. The information recording device according to claim 9, in which said change detection means is further operable to learn from a previous observed value or values so as to form a class or classes.

11. The information recording device according to claim 9, in which said change detection means is further operable to generate the feature space from learning involving a respective observed value or values and a respective class or classes associated therewith.

12. A information recording method comprising:
   a step of measuring bio-information of a person and/or environmental information around said person;
   a step of detecting changes in said bio-information and/or said environmental information measured by the measuring step;
   a step of recording said bio-information and/or said environmental information; and
   a step of controlling the recording step,
   the step of detecting change includes detecting changes in said bio-information and/or said environmental information by use of pattern recognition which includes classifying a number of subjects into a number of classes, and mapping an observed value of said bio-information and/or said environmental information into a class in a feature space.

13. The information recording method according to claim 12, in which the step of detecting change further includes learning from a previous observed value or values so as to form a class or classes.

14. The information recording method according to claim 12, in which the step of detecting change further includes generating the feature space from learning involving a respective observed value or values and a respective class or classes associated therewith.

* * * * *